United States Patent [19]

Fischer

[11] Patent Number: 4,987,234

[45] Date of Patent: Jan. 22, 1991

[54] PROCESS FOR THE PREPARATION OF CYCLIC UREAS

[75] Inventor: Hartmut Fischer, Hofheim am Taunus, Fed. Rep. of Germany

[73] Assignee: Hoechst Aktiengesellschaft, Frankfurt, Fed. Rep. of Germany

[21] Appl. No.: 393,999

[22] Filed: Aug. 15, 1989

[30] Foreign Application Priority Data

Aug. 17, 1988 [DE] Fed. Rep. of Germany ....... 3827867

[51] Int. Cl.$^5$ ............................................ C07D 487/00
[52] U.S. Cl. .................................................. 548/305
[58] Field of Search ....................................... 548/305

[56] References Cited

U.S. PATENT DOCUMENTS

| | | | |
|---|---|---|---|
| 3,414,619 | 12/1968 | Cross et al. | 548/305 |
| 3,853,708 | 12/1974 | Porath et al. | 548/305 |
| 4,070,348 | 1/1978 | Kraemer et al. | 548/305 |
| 4,190,713 | 2/1980 | Kraemer et al. | 548/305 |
| 4,208,309 | 6/1980 | Kraemer et al. | 548/305 |
| 4,282,193 | 4/1981 | Melchior et al. | 548/305 |
| 4,282,194 | 4/1981 | Say et al. | 548/305 |
| 4,415,700 | 11/1983 | Batz et al. | 548/305 |
| 4,511,694 | 4/1985 | Kramer et al. | 548/305 |
| 4,582,860 | 4/1986 | Bigwood et al. | 548/305 |
| 4,612,288 | 9/1986 | Bigwood et al. | 548/305 |
| 4,772,635 | 9/1988 | Mitschker et al. | 548/305 |

FOREIGN PATENT DOCUMENTS

| | | | |
|---|---|---|---|
| 0013859 | 6/1980 | European Pat. Off. | 548/305 |
| 0054685 | 6/1982 | European Pat. Off. | 548/305 |
| 0058767 | 9/1982 | European Pat. Off. | 548/305 |
| 0146329 | 6/1985 | European Pat. Off. | 548/305 |
| 1543748 | 12/1969 | Fed. Rep. of Germany | 548/305 |
| 2102514 | 7/1971 | Fed. Rep. of Germany | 548/305 |
| 2237316 | 2/1974 | Fed. Rep. of Germany | 548/305 |
| 2722751 | 11/1978 | Fed. Rep. of Germany | 548/305 |
| 3124618 | 3/1982 | Fed. Rep. of Germany | 548/305 |
| 1343703 | 1/1974 | United Kingdom | 548/305 |
| 1431940 | 4/1976 | United Kingdom | 548/305 |
| 1598050 | 9/1981 | United Kingdom | 548/305 |

OTHER PUBLICATIONS

Ind. Eng. Chem. Res. 1987, 26, 1056–1059.
Indian J. Technol., 1969, vol. 7, 111–114.

*Primary Examiner*—Mary C. Lee
*Assistant Examiner*—Robert C. Whittenbaugh

[57] ABSTRACT

A process for the preparation of cyclic urea derivatives of the formula

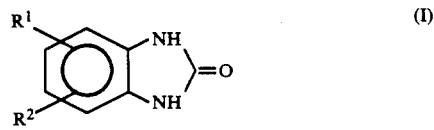

(I)

in which $R^1$ and $R^2$ are equal or different and represent hydrogen, alkyl having from 1 to 6 carbon atoms or alkoxy having from 1 to 3 carbon atoms, which comprises reacting a 1,2-diaminobenzene of the formula

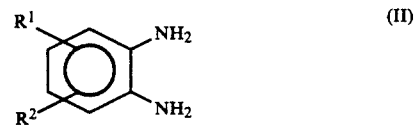

(II)

in which $R^1$ and $R^2$ have the meaning indicated above are reacted with carbon dioxide in the presence of water under superatmospheric pressure at a temperature of at least 120° C.

29 Claims, No Drawings

PROCESS FOR THE PREPARATION OF CYCLIC UREAS

The invention relates to the preparation of cyclic ureas. Today these are prepared on an industrial scale by reaction of the corresponding diaminoaromatics, in the simplest case the o-phenylenediamine, with carbonic acid derivatives such as urea or phosgene. The disadvantage of this process is the unavoidable formation of considerable amounts of ammonium salts and, if phosgene is used, the handling of this toxic substance.

There has not been a lack of attempts to synthesize cyclic ureas directly from diamino compounds and carbon dioxide. This reaction could only be achieved with incomplete conversion despite the application of high pressures and temperatures. It is true that the yield could be improved by addition of water-binding agents, such as dicyclohexylcarbodiimide, but it still remained unsatisfactory. A further improvement has been described by R. Nomura, M. Yamamoto and H. Matsuda (Ind. Eng. Chem. Res. 1987, 1056–1059), who recognized that triphenyl stibine oxide is an effective catalyst for the reaction. However, the catalytic effect has only been proven for the reaction of aliphatic diamines and moreover the use of this organometallic compound in an industrial process is not advantageous, and therefore this route was not pursued further.

German Offenlegungsschrift 1,543,748 (=U.S. Pat. Nos. 3,413,350 and 3,414,619) discloses the reaction of aromatic o-diamines with $CO_2$, preferably in the presence of alkali metal or alkaline earth metal compounds, thus removing the o-diamines from mixtures which predominantly contain p-isomers. The basic alkali metal and alkaline earth metal compounds mentioned include, in addition to many others, also sodium carbonate, potassium carbonate and even calcium carbonate. German Offenlegungsschrift 1,543,748 also mentions that supposedly the amount of o-diamine present in the isomeric mixtures is not important, that small amounts as well as fairly large amounts are removed, and even 100% pure aromatic o-diamines can be reacted with carbon dioxide. However, as shown by inhouse tests, this reaction is unsuitable for the conversion of pure o-diamines to benzimidazolones, because it proceeds only very slowly and in particular because the reaction mixture after the formation of a fairly large amount of cyclic urea, becomes so viscous, due to the high melting points, that it can no longer be stirred, this situation arising at conversions between 30 and 50%. This means that the high melting point and the low solubility of the final products make it difficult to carry out this reaction in industrial practice because even at low degrees of conversion it is no longer possible to stir the mixture and to move and discharge the solid.

It was therefore desirable to develop a simple and trouble-free process for the reaction of ortho-diamines with $CO_2$. However, this made it necessary to find a suitable liquid reaction medium in which, on the one hand, the reaction proceeds smoothly and which on the other hand makes it possible, to discharge the product from the reactor. In the search for such a suitable liquid reaction medium, it turned out that all obvious organic solvents such as alcohols, ethers, amines or amides are not suitable solvents for the product or inhibit the reaction.

Surprisingly, it has now been found that the synthesis of cyclic ureas from orthodiamines and $CO_2$ is possible in aqueous systems and is even particularly successful therein.

This result is all the more surprising, since water as a reaction product of the urea formation was expected to hinder the synthesis. In an article in Indian J. Technol. 1969, 111–114, T.V. Charlu and M.R.A. Rao regarded the effect of the water of the reaction on the yield in the synthesis of imidazolones from 1,2-diamines and $CO_2$ as detrimental (see summary). Accordingly, methods to remove the interfering water, for example by addition of carbodiimides or $PCl_3$, are also known from the literature.

The invention relates to a process for the preparation of cyclic ureas of the structure type of benzimidazolones I (see patent claim 1) in which $R^1$ and $R^2$, independently of one another, are hydrogen, alkyl having 1 to 6 carbon atoms or alkoxy having 1 to 3 carbon atoms by reaction of the corresponding diamino compound II (see patent claim 1) with carbon dioxide, if appropriate in the presence of catalysts, which comprises carrying out the reaction in the presence of water as reaction medium under superatmospheric pressure at a temperature of at least 120° C. The use of water turns out to be extremely advantageous, because the process, due to the permanent presence of the liquid medium water, remains technically feasible even on a large scale. Virtually no by-products are formed even on a large scale. The separation of product, reaction medium, catalyst and any small amounts of remaining starting material (1,2-diamine) can be achieved by simple filtration and washing with water; water, catalyst and remaining starting material can be recycled into the process as often as desired, so that the desired products of the formula I can be prepared without any problems of waste disposal.

The process can be used for starting materials of the structure II in which $R^1$ and $R^2$ are either hydrogen atoms or lower alkyl radicals such as methyl, ethyl or the various propyl, butyl, pentyl or hexyl radicals, or alkoxy radicals having 1 to 3 carbon atoms, preferably only one of the radicals being alkoxy. The alkyl radicals advantageously contain 1 to 4, in particular 1 or 2 carbon atoms, and the alkoxy radicals preferably 1 to 2 carbon atoms, in particular only 1 carbon atom. Very particularly preferred starting materials are those in which at least one of the radicals $R^1$ and $R^2$ is hydrogen, in particular, 1,2-diaminobenzene and the two 1,2-diaminotoluenes.

The process according to the invention has to be carried out in a pressure reactor. The starting materials can be initially introduced as aqueous solution at standard pressure or can even be introduced under pressure via a pump. The carbon dioxide is advantageously introduced via a metering device under pressure in liquid or gaseous form, which makes it possible to operate the pressure reactor, while utilizing most of the volume, and even to operate it continuously.

Relative to the diamino compound, the amount of water used can be varied within wide limits. For example, between 20 and 800, for example up to 500, % by weight of water, relative to the diamino compound, are used. Preferably, the reaction is carried out with amounts of water between 50 and 400, often up to 300, % by weight. This makes it possible to obtain homogeneous solutions of the starting materials at elevated temperature; a very high conversion of more than 95% is achieved, and the product formed is an aqueous suspension of the cyclic urea which is easy to stir and to move, which is very advantageous for carrying out the process in industry, given the low solubility and the high melting point of the compounds II.

The reaction of the diamino compound with $CO_2$ is accelerated by basic water-soluble compounds, the use of which makes it possible to achieve conversions on a particularly large scale. Therefore it is advantageous to add such bases to the reaction medium water. The amount is in general between 2 and 100, often up to 30, mol %, relative to the diamino compound; preferably, 10 to 50, often up to 25, mol% of the basic catalyst are added. Suitable basic catalysts are in particular basic alkali metal compounds, for example the carbonates, bicarbonates and hydroxides of the alkali metals, such as sodium, in particular potassium, ammonium carbonate and aqueous ammonia solution; organic bases such as trialkylamines, for example triethyl-, tri-n- or -isopropyl amines or the various tributylamines or triamines having different alkyl radicals, or morpholine are also suitable. A catalyst which is used particularly preferably is potassium carbonate, because it is particularly effective, can readily be removed from the product by washing and recycled completely.

The reaction temperature is advantageously between 150° and 260° C. Increasing reaction temperature accelerates the reaction, but excessively high temperature decreases the selectivity. The optimum and most preferred temperature range is between 200 and 240° C.

The carbon dioxide can initially be used in large excess, for example twice the molar amount. It is also possible to begin with a slight excess or even with less than the molar amount, if during the reaction the $CO_2$ consumed is continuously reintroduced. It should be noted that the total pressure of the system is composed of the partial pressure of the water vapor, which depends on the temperature, and the $CO_2$ partial pressure, which is a result of the $CO_2$ amount introduced or still present. The minimum partial pressure of $CO_2$ at the reaction temperature should not be less than 1 bar. The partial pressure can be, for example, up to 200 bar; advantageously, it is maintained between 5 and 50 bar. Preferably, a $CO_2$ pressure of 10 to 30 bar is maintained during the reaction phase. This leads to a total pressure of 25 to 64 bar in the preferred temperature range between 200 and 240° C. Advantageously the pressure vessel should be at least designed for this pressure. After the reaction is completed, the mixture is cooled to a temperature below 100° C., during which the mixture obtained is advantageously slowly stirred, in order to distribute the crystallizing cyclic urea in finely divided form in the aqueous reaction medium. In this form, the product can be removed from the reactor, after the excess carbon dioxide pressure has been let down. The separation from the aqueous reaction medium, for example the catalyst solution, can be effected very easily by filtration. The liquid which may contain a catalyst together with remaining unconverted diamino compound can be recycled into the process. The process is therefore distinguished by a significantly reduced pollution of the effluent.

EXAMPLES 1. 43.2 g. (0.4 mol) of 1,2-diaminobenzene and a solution of 11 g. (0.08 mol) of potassium carbonate in 54 g of water were initially introduced into a pressure reactor of 200 ml capacity. The closed reactor was then filled with $CO_2$ up to a pressure of 30 bar and brought to the reaction temperature by means of electrical heating. This initially raised the total pressure to reach a maximum value of 62 bar in the heating phase at 180° C., which then slowly dropped again as a result of the start of the reaction. Heating was then continued. After a total pressure of 40 bar had been established at the constant reaction temperature of 230° C., this pressure was kept constant for 6 hours by additional injection of $CO_2$. The mixture was then cooled, and the remaining $CO_2$ pressure let down.

The benzimidazolone which was suspended in the catalyst solution was removed from the opened pressure reactor and separated off from the solution by filtration. (After the losses had been replenished, this solution can be recycled into the reactor for the next batch.) The benzimidazolone was washed on the filter with 50 ml of water and then dried. The material was very crystalline, had a light gray-blue color and a melting point of 318° C. Yield: 48.9 g. = 91.2% of theory.

2. 1080 g. (10 mol) of 1,2-diaminobenzene, 276 g. (2 mol) of $K_2CO_3$ and 1700 g. of water were mixed and made into a homogeneous solution by heating to 90° C., which was transferred to a preheated pressure reactor of a volume of 10 l. 1000 g. (23 mol) of $CO_2$ were then pumped in, and the temperature was increased to 230° C. and maintained for 6 hours. During the heating period, the pressure rose to a maximum of 55 bar. After the reaction was completed, the mixture was cooled, the excess $CO_2$ pressure was let down, and the reaction product removed. The benzimidazolone formed was separated from the solution containing the catalyst in a pressure filter, and the filter cake was washed with 300 g of water to remove any adhering remaining catalyst solution from the product. The recovered catalyst solution which still contained a small amount of unconverted 1,2-diaminobenzene was recycled into the process. In the example described here, the catalyst solution was recycled twice; the individual results are summarized in the table.

3. 24.4 g (0.2 mol) of 3,4-diaminotoluene, 18 g of water and 5.5 g (0.04 mol) of potassium carbonate were introduced into a 200 ml reactor. After sealing, $CO_2$ was injected up to a pressure of 35 bar. The mixture was then heated to 230° C., and this temperature maintained for 12 hours. During the heating period, the pressure rose to up to 80 bar. After the reaction was completed, the mixture was cooled, the excess $CO_2$ pressure was let down, and the aqueous slurry of crystals was removed. The aqueous catalyst solution was separated off through a filter, the solid was washed with water until it no longer contained carbonate, and was dried. 27.7 g (93.7% of theory) of 5-methylbenzimidazolone of m.p. = 301–303° C. were isolated.

4. Example 3 was repeated, except that 27.3 g (0.2 mol) of 4,5-diamino-ortho-xylene were used instead of 3,4-diaminotoluene. After workup of the mixture, 31.3 g (96% of theory) of 5,6-dimethylbenzimidazolone (m.p. above 360° C.) were isolated.

5. Example 3 was repeated, using 27.6 g (0.2 mol) of 3,4-diaminoanisole as starting material. 30.5 g (93.0% of theory) of 5-methoxybenzimidazolone of m.p. 256° C. were isolated as the product.

6. 43.2 g (0.4 mol) of 1,2-diaminobenzene, 54 g of water and 7.7 ml of a concentrated aqueous ammonia solution (corresponding to 0.1 mol of $NH_3$) were placed in a pressure reactor of 200 ml capacity. The reactor was then charged with $CO_2$ up to a pressure of 40 bar. During the heating period, the pressure rose to a maximum of 80 bar and, after reaching the reaction temperature of 210° C., slowly dropped again. A constant pressure of 50 bar was maintained for 12 hours by additional injection $CO_2$. The mixture was then cooled, and the remaining $CO_2$ pressure let down. The product was removed, filtered off from the catalyst solution, washed with 50 ml of water and dried. The yield of benzimidazolone was 46.6 g =87.0% of theory. The fact that the yield is less than in Examples 1 to 5 does not have any great practical significance, simply for the reason that unconverted diamine and the aqueous reaction medium, after the desired product has been separated off, can be recycled into the production process.

7. and 8. Example 6 was repeated, except that 8.7 g (0.1 mol) of morpholine were used as catalyst instead of the aqueous ammonia solution. After workup, 41.9 g. = 78.2% of theory of benzimidazolone were isolated. A similar result was obtained by using a 10.1 g. (0.1 mol) of triethylamine as catalyst.

| Table for Examples 2a–c |||||||||
|---|---|---|---|---|---|---|---|---|
| Water | $K_2CO_3$ | Amount of $Ph(NH_2)_2$ used | Filtrate + wash water | Amount of $PH(NH_2)_2$ left || from experiment | Benzimidazolone isolated, dried ||
| g | g | g | g | g | % | | | |
| a | 1700 | 276 | 1080 | | | | | 1250 | 93.3 |
| b | | | 1125 | 1980 | 18 = | 1.7 | a | 1298 | 91.5 |
| c | | | 1136 | 1980 | 35 = | 3.2 | b | 1328 | 92.2 |
| | | | | 1980 | 37 = | 3.3 | c | | |

9. Example 1 was repeated, except that the molar ratio of water and alkaline carbonate to diamino compound was increased. 21.6 g (0.2 mol) 1,2-diaminobenzene, 108 g of water and 27.6 g (0.2 mol) of potassium carbonate were placed in a pressure reactor of 200 ml capacity. The reactor was sealed, and at about 50° C. of internal temperature $CO_2$ was introduced to a pressure of 35 bar. The mixture was then heated to a reaction temperature of 230° C., during which the pressure reached 65 bar for a short time, but slowly dropped after the start of the reaction. The pressure was maintained at 58 to 60 bar for 6 hours by additional injection of $CO_2$. The mixture was then cooled to room temperature, and excess $CO_2$ was flushed out. The suspension of the product was removed from the pressure-free reactor, and the benzimidazolone was isolated by filtration. Washing and drying gave 24.0 g (89.6% of theory) of benzimidazolone.

10. As in Example 9, 21.6 g (0.2 mol) of 1,2-diaminobenzene in 108 g of water were used, but 21.2 g (0.2 mol) of $Na_2CO_3$ were added as $CO_2$ transferring agent. The reaction with $CO_2$ was carried out at 210° C. for 6 hours at a total pressure of 58 to 62 bar. After the reaction was completed (pressure remaining constant), the mixture was cooled to 130° C., and excess $CO_2$ pressure was let down at this temperature. This was continued until the gas phase of the system largely consisted of water vapor. This measure prevented the crystallization of sodium bicarbonate upon cooling to room temperature, and only the almost colorless finely crystalline benzimidazolone was suspended in the sodium carbonate solution and isolated by filtration. Yield: 24.4 g (91.0% of theory).

11. The procedure was repeated analogously to Example 10, but a smaller amount of a less concentrated sodium carbonate solution was used as the reaction medium. 21.6 g (0.2 mol) of 1,2-diaminobenzene, 90 g of water and 10.6 g (0.1 mol) of sodium carbonate were placed in the reactor. The reaction with $CO_2$ was carried out at 210° C. over 6 hours at a total pressure of 58 to 62 bar. After the $CO_2$ pressure had been let down at 130° C., cooling to room temperature was continued, and the benzimidazolone was isolated. Yield: 22.5 g (84.0% of theory).

I claim:

1. A process for the preparation of cyclic urea derivatives of the formula

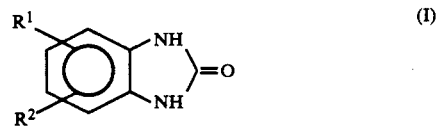

(I)

in which $R^1$ and $R^2$ are equal or different and represent hydrogen, alkyl having from 1 to 6 carbon atoms or alkoxy having from 1 to 3 carbon atoms, which comprises reacting a 1,2-diaminobenzene of the formula

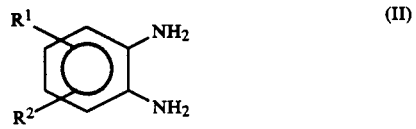

(II)

in which $R^1$ and $R^2$ have the meaning indicated above are reacted with carbon dioxide in the presence of water as the reaction medium under superatmospheric pressure at a temperature of at least 120° C.

2. A process as claimed in claim 1, wherein the amount of water applied is in the range of from 20 to 800% by weight, referred to the diamino compound.

3. A process as claimed in claim 2, wherein the amount of water applied is in the range of from 20 to 500% by weight, referred to the diamino compound.

4. A process as claimed in claim 3, wherein the amount of water applied is in the range of from 50 to 400% by weight, referred to the diamino compound.

5. A process as claimed in claim 4, wherein the amount of water applied is in the range of from 50 to 300% by weight, referred to the diamino compound.

6. A process as claimed in claim 1, wherein the reaction is carried out in the presence of a water-soluble basic compound as a catalyst.

7. A process as claimed in claim 1, wherein the reaction is carried out in the presence of from 2 to 100 mol-% of a basic, water-soluble catalyst, referred to the diamino compound.

8. A process as claimed in claim 7, wherein the reaction is carried out in the presence of from 10 to 50 mol-% of a basic, water-soluble catalyst, referred to the diamino compound.

9. A process as claimed in claim 7, wherein the reaction is carried out in the presence of from 10 to 25 mol-% of a basic, water-soluble catalyst, referred to the diamino compound.

10. A process as claimed in claim 6, wherein the water-soluble basic compound is an alkali metal compound.

11. A process as claimed in claim 6, wherein the water-soluble basic compound is potassium carbonate.

12. A process as claimed in claim 1, wherein the reaction is carried out at a temperature in the range of from 150 to 260° C.

13. A process as claimed in claim 12, wherein the reaction is carried out at a temperature in the range of from 200 to 240° C.

14. A process as claimed in claim 1, wherein the carbon dioxide is added in the initial phase of the reaction in at least double of the molar amount.

15. A process as claimed in claim 1, wherein the reaction is carried out using a carbon dioxide partial pressure of at least 1 bar and up to 200 bar.

16. A process as claimed in claim 15, wherein the reaction is carried out at a pressure in the range of from 5 to 5 bar.

17. A process as claimed in claim 16, wherein the reaction is carried out at a pressure in the range of from 10 to 3 bar.

18. A process as claimed in claim 1, wherein carbon dioxide is continuously added to the reaction system during the reaction.

19. A process as claimed in claim 1, wherein any alkyl groups have from 1 to 4 carbon atoms.

20. A process as claimed in claim 1, wherein any alkyl groups have from 1 to 2 carbon atoms.

21. A process as claimed in claim 1, wherein any alkoxy groups have from 1 to 2 carbon atoms.

22. A process as claimed in claim 21, wherein any alkoxy group has one carbon atom.

23. A process as claimed in claim 1, wherein at most one of $R^1$ and $R^2$ is alkoxy.

24. A process as claimed in claim 1, wherein a compound II is reacted in which at least one of the groups $R^1$ and $R^2$ represents hydrogen.

25. A process as claimed in claim 24, wherein a 1,2-diaminotoluene is reacted.

26. A process as claimed in claim 24, wherein 1,2-diaminobenzene is reacted.

27. A process for the preparation of cyclic urea derivatives of the formula

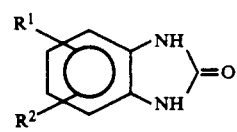

(I)

in which $R^1$ and $R^2$ are equal or different and represent hydrogen, alkyl having from 1 to 4 carbon atoms or alkoxy having from 1 to 2 carbon atoms, which comprises reacting a 1,2-diaminobenzene of the formula

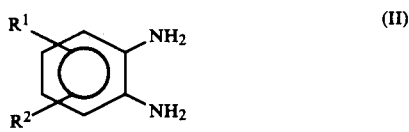

(II)

in which $R^1$ and $R^2$ have the meaning indicated above are reacted with carbon dioxide in the presence of from 20 to 800% by weight, referred to the diamino compound, of water under superatmospheric pressure using a carbon dioxide partial pressure in the range from 1 to 200 bar at a temperature in the range of from 150 to 260° C. and in the presence of a basic, water-soluble compound as a catalyst.

28. A process for the preparation of cyclic urea derivatives of the formula

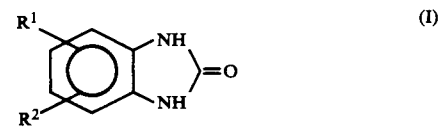

(I)

in which $R^1$ and $R^2$ are equal or different and represent hydrogen, alkyl having from 1 to 4 carbon atoms or alkoxy having from 1 to 2 carbon atoms, which comprises reacting a 1,2-diaminobenzene of the formula

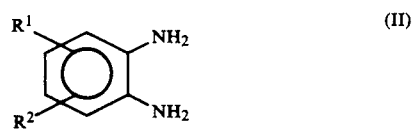

(II)

in which $R^1$ and $R^2$ have the meaning indicated above are reacted with carbon dioxide in the presence of from 20 to 800% by weight, referred to the diamino compound, of water under superatmospheric pressure using a carbon dioxide partial pressure in the range from 1 to 200 bar at a temperature in the range of from 150 to 260° C. and in the presence of a basic, water-soluble compound as a catalyst, separating the cyclic urea formed by filtration from the aqueous reaction medium and recycling the liquid into the reaction system.

29. A process as claimed in claim 27, wherein the basic, water-soluble compound acting as catalyst is sodium carbonate.

* * * * *

UNITED STATES PATENT AND TRADEMARK OFFICE
CERTIFICATE OF CORRECTION

PATENT NO. : 4,987,234
DATED : January 22, 1991
INVENTOR(S) : Hartmut Fischer

It is certified that error appears in the above-identified patent and that said Letters Patent is hereby corrected as shown below:

In claim 16, col. 7, line 29
"5 to 5 bar" should read
-- 5 to 50 bar--.
In claim 17, col. 7, line 32
"10 to 3 bar" should read
--10 to 30 bar--.

Signed and Sealed this

Thirty-first Day of March, 1992

Attest:

HARRY F. MANBECK, JR.

Attesting Officer     Commissioner of Patents and Trademarks